US012805855B2

(12) United States Patent
Maracaja et al.

(10) Patent No.: US 12,805,855 B2
(45) Date of Patent: Nov. 24, 2026

(54) DEVICE AND METHOD FOR MANAGEMENT OF DELAYED CHEST CLOSURE

(71) Applicant: Duke University, Durham, NC (US)

(72) Inventors: Luiz Maracaja, Durham, NC (US); Carmelo Milano, Durham, NC (US)

(73) Assignee: Duke University, Durham, NC (US)

( * ) Notice: Subject to any disclaimer, the term of this patent is extended or adjusted under 35 U.S.C. 154(b) by 83 days.

(21) Appl. No.: 18/660,889

(22) Filed: May 10, 2024

(65) Prior Publication Data

US 2024/0374248 A1 Nov. 14, 2024

Related U.S. Application Data

(60) Provisional application No. 63/466,047, filed on May 12, 2023.

(51) Int. Cl.
*A61B 17/02* (2006.01)
*A61B 17/80* (2006.01)

(52) U.S. Cl.
CPC ...... *A61B 17/0206* (2013.01); *A61B 17/0218* (2013.01); *A61B 17/8076* (2013.01)

(58) Field of Classification Search
CPC ... A61B 1/32; A61B 17/0206; A61B 17/0218; A61B 17/8076; A61B 6/0492; A61B 17/02; A61B 2017/0237
USPC .................................................. 600/201–245
See application file for complete search history.

(56) References Cited

U.S. PATENT DOCUMENTS 2,450,194 A * 9/1948 Glaser ................ A61B 17/0206 600/232
4,726,356 A * 2/1988 Santilli .............. A61B 17/0206 600/234

(Continued)

FOREIGN PATENT DOCUMENTS

CA 3081187 A1 * 5/2019 ......... A61B 17/0206
CA 2853106 C 11/2021

(Continued)

OTHER PUBLICATIONS

Bakaeen et al., "Advances in managing the noninfected open chest after cardiac surgery: Negative-pressure wound therapy," J Thorac Cardiovasc Surg, 2019, 157(5): 1891-1903.e9.

(Continued)

*Primary Examiner* — Eduardo C Robert
*Assistant Examiner* — Tara Rose E Carter
(74) *Attorney, Agent, or Firm* — Casimir Jones, S.C.; Thomas J. Lyneis

(57) ABSTRACT

A thoracic device including a pair of sternal plates, each sternal plate of the pair of sternal plates including a body having a first end and a second end, a first arm extending from the first end of the body, the first arm having a cavity oriented transverse to the body and an aperture oriented parallel to the body, and a second arm extending from the second end of the body. The thoracic device includes a bar including a third end and a fourth end, the third end having a first channel and the fourth end having a second channel. The third end of the bar is received within the cavity of one of the pair of sternal plates and the fourth end of the bar is received within the cavity of the other one of the pair of sternal plates.

20 Claims, 14 Drawing Sheets

(56) References Cited

U.S. PATENT DOCUMENTS

| | | | | |
|---|---|---|---|---|
| 7,338,434 | B1 * | 3/2008 | Haarstad .......... | A61B 17/00234 600/235 |
| 10,993,766 | B2 | 5/2021 | Anderson et al. | |
| 2004/0225197 | A1 * | 11/2004 | Roux ................. | A61B 17/0206 600/231 |
| 2007/0161865 | A1 * | 7/2007 | Fakhrai ............. | A61B 17/0206 600/231 |
| 2011/0251540 | A1 * | 10/2011 | Notrica ............. | A61B 17/8076 602/19 |
| 2015/0327847 | A1 * | 11/2015 | Fehling ............. | A61B 17/0206 600/215 |
| 2019/0307442 | A1 * | 10/2019 | Sauer ................. | A61B 17/0469 |
| 2020/0253594 | A1 * | 8/2020 | Wilson ............... | A61B 17/7074 |

FOREIGN PATENT DOCUMENTS

| | | | | |
|---|---|---|---|---|
| EP | 2953563 B1 | | 10/2023 | |
| WO | WO-2005016131 A2 | * | 2/2005 | ............. A61B 17/02 |
| WO | WO-2011099553 A1 | * | 8/2011 | ......... A61B 17/0206 |

OTHER PUBLICATIONS

Boeken et al., "Open chest management after cardiac operations: outcome and timing of delayed sternal closure," Eur J Cardiothorac Surg, 2011, 40(5): 1146-50.

Karsan et al., "Minimally-invasive cardiac surgery: a bibliometric analysis of impact and force to identify key and facilitating advanced trainin," J Cardiothorac Surg, 2022, 17: 236.

Kim et al., "Commentary: Open Your Mind to Open Chest Management," J Chest Surg, 2023 56(3): 213-215.

Senst et al., "Cardiac Surgery," StatPearls, Available from: <https://www.ncbi.nlm.nih.gov/books/NBK532935/> Last Update: Sep. 12, 2022.

Takayama et al., "Open-Chest Management after Heart Transplantation," Tex Heart Inst J, 2006, 33(3): 306-309.

Vervoort et al., "Global cardiac surgery: Access to cardiac surgical care around the world," The Journal of Thoracic and Cardiovascular Surgery, 2020, 159(3): 987-996.e6.

* cited by examiner

DEVICE AND METHOD FOR MANAGEMENT OF DELAYED CHEST CLOSURE

CROSS-REFERENCE TO RELATED APPLICATIONS

This application is a non-provisional of and claims the benefit of U.S. Provisional Patent Application No. 63/466,047, filed May 12, 2023, the entire contents of which are incorporated herein by reference.

FIELD OF THE DISCLOSURE

The present disclosure relates to a device used for delayed chest closure. More particularly, the present disclosure relates to a device to keep the chest cavity open for a period of time after cardiac surgery and thoracic surgery.

SUMMARY OF THE DISCLOSURE

The present disclosure provides, in one aspect, a thoracic device including a pair of sternal plates, each sternal plate of the pair of sternal plates including a body having a first and a second end, a first arm extending from the first end of the body, the first arm having a cavity oriented transverse to the body and an aperture oriented parallel to the body, and a second arm extending from the second end of the body. The thoracic device includes a bar including a third end and a fourth end, the third end having a first channel and the fourth end having a second channel. The third end of the bar is received within the cavity of one of the pair of sternal plates and the fourth end of the bar is received within the cavity of the other of the pair of sternal plates.

The present disclosure provides, in another aspect, a kit including a first pair of sternal plates. Each of the first pair of sternal plates include a body having a first end and a second end, the body having a first length. Each of the first pair of sternal plates include a first arm extending from the first end of the body, the first arm having a cavity oriented transverse to the body and an aperture oriented parallel to the body, and a second arm extending from the second end of the body. The kit includes a plurality of bars, each bar having a different length. Each bar includes a third end and a fourth end, the third end having a first channel and the fourth end having a second channel. The third end of the bar is received within the cavity of one of the first pair of sternal plates and the fourth end of the bar is received within the cavity of the other of the first pair of sternal plates.

In some embodiments, the thoracic device is used to space apart a chest of the patient in a post-operative setting. For example, the thoracic device may be considered as a spacer. The thoracic device permits easy access to the chest of the patient. The thoracic device stabilizes the chest of the patient. In some instances, the thoracic device allows for less sedation of the patient due to the increased stabilization of the chest of the patient. In some instances, the thoracic device enables less vasopressor drug support. The thoracic device provides additional space for organ recovery (e.g., heart recovery). The sternal plates of the thoracic device receive sternal edges of the patient and block bleeding from the sternal edges (e.g., tamponade bone marrow bleeding). The sternal plates of the thoracic device include smooth surfaces and edges that interface with the chest of the patient. The smooth surfaces and edges prevent additional damage and irritation to the chest of the patient. The thoracic device aids in radiographic positioning of the patient with radiopaque markers. The thoracic device includes a profile relative to the chest such that the chest cavity may be covered. For instance, the chest can be covered with a biocompatible material sutured to the skin and covering the whole incision.

Other features and aspects of the disclosure will become apparent by consideration of the following detailed description and accompanying drawings.

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways.

DETAILED DESCRIPTION

Figure 1:
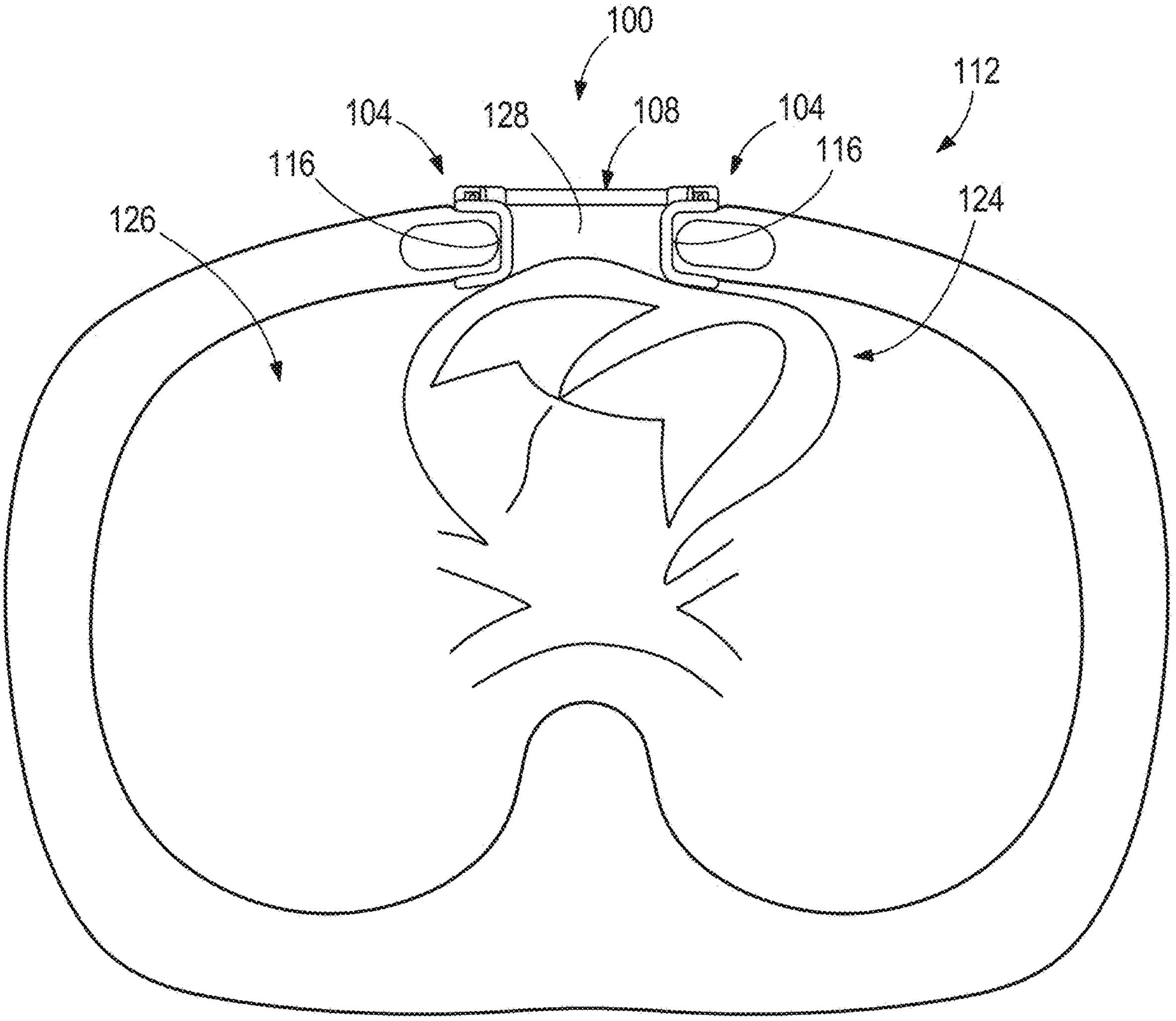
FIG. 1 is a schematic view of a thoracic device, according to an embodiment of the disclosure.

FIG. 1 illustrates a schematic view of a thoracic device 100 (thoracic device may also be referred to as a chest device herein) according to an embodiment of the disclosure. The thoracic device 100 includes a pair of sternal plates 104 and a bar 108. The thoracic device 100 holds a chest 112 of a patient open for prolonged periods of time. Specifically, each sternal plate of the sternal plates 104 maintains a distance between opposing sternal edges 116 of the sternum of the patient. In the illustrated embodiment, the sternal edges 116 are separated by an incision that is parallel to the chest 112. In other embodiments, each sternal plate of the sternal plates 104 maintains a distance between opposing sternal edges 116 when the sternal edges 116 are separated by an incision that is transverse to the chest 112.

As exaggerated in FIG. 1, a heart 124 of the patient may swell, which is known as myocardial edema. The swelling of the heart 124 may be attributed to prolonged operations, perfusion time, and poor myocardial preservation. If the heart becomes dilated, edematous, and stunned, there will be an increase in its physical size, which will require more space inside a chest cavity 126 of the chest 112 (e.g., mediastinum) to maintain function. As such, opening the chest 112 increases cardiac index and systemic blood pressure without significantly changing cardiac filling pressure. The thoracic device 100 holds the chest 112 open and also provides a space 128 for the swelling of the heart 124. Although FIG. 1 illustrates the thoracic device 100 being used with the heart 124 after heart surgery, the thoracic device 100 may be used after other operations of the chest cavity, such as a lung transplant.

Figure 2:
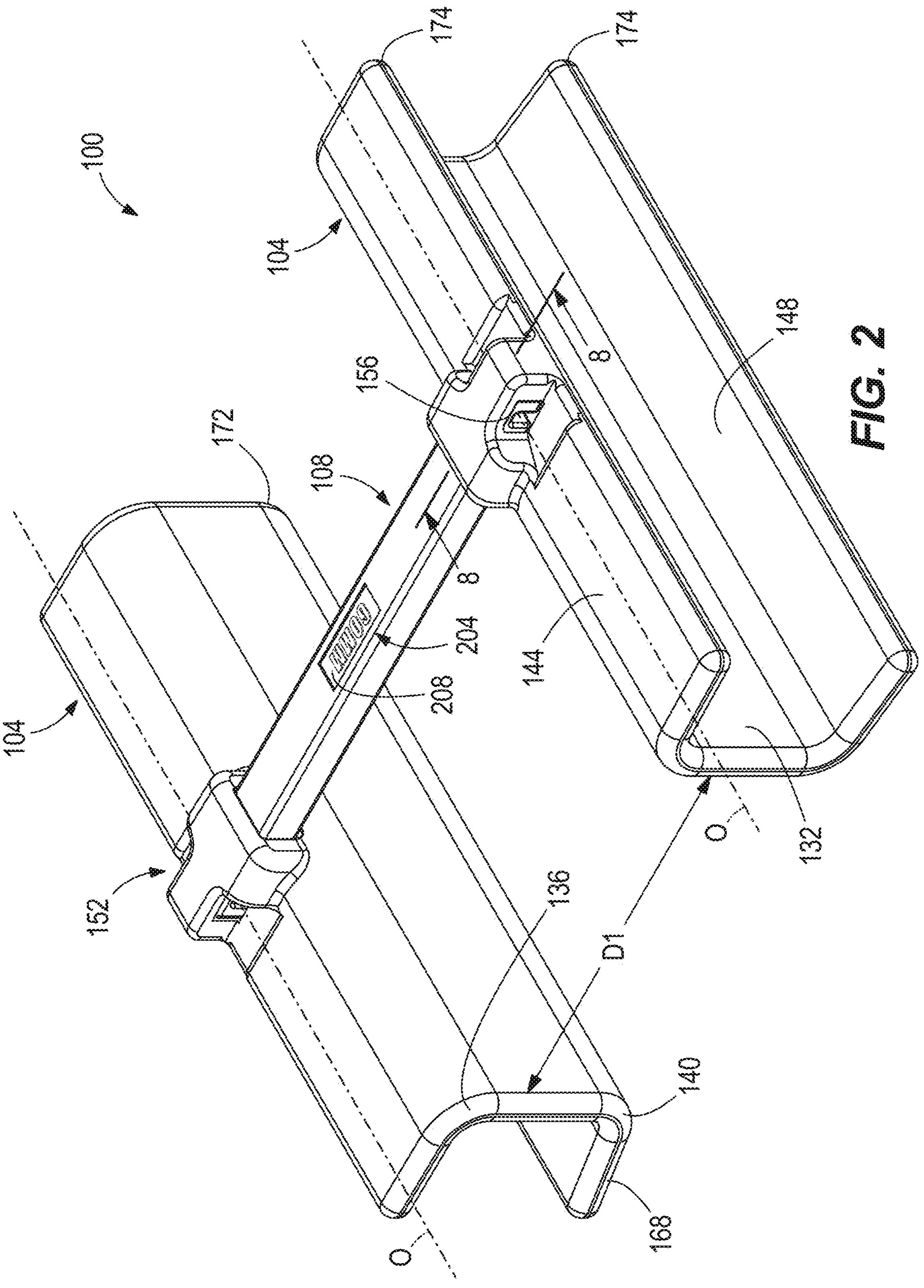
FIG. 2 is a front perspective view of the thoracic device of FIG. 1.

FIG. 2 illustrates the pair of sternal plates 104 receiving the bar 108. In the illustrated embodiment, the pair of sternal plates 104 and the bar 108 are comprised of a glass reinforced polymer (e.g., a glass-fiber reinformed, general purpose polyarylamide compound, such as Ixef® 1022). In other embodiments, the pair of sternal plates 104 and the bar 108 are comprised of a metal. Each sternal plate of the pair of sternal plates 104 includes a body 132 having a first end 136 and a second end 140. Each sternal plate of the pair of sternal plates 104 includes a first arm 144 extending from the first end 136 of the body 132 and a second arm 148 extending from the second end 140 of the body 132. The first arm 144 includes a cavity 152 that is oriented transverse to the body 132 and an aperture 156 that is oriented parallel to the body 132. The bar 108 includes a third end 160 and fourth end 164. The third end 160 is received within the cavity 152 of one sternal plate of the pair of sternal plates 104 and the fourth end 164 is received within the cavity 152 of the other of the pair of sternal plates 104.

Figure 3:
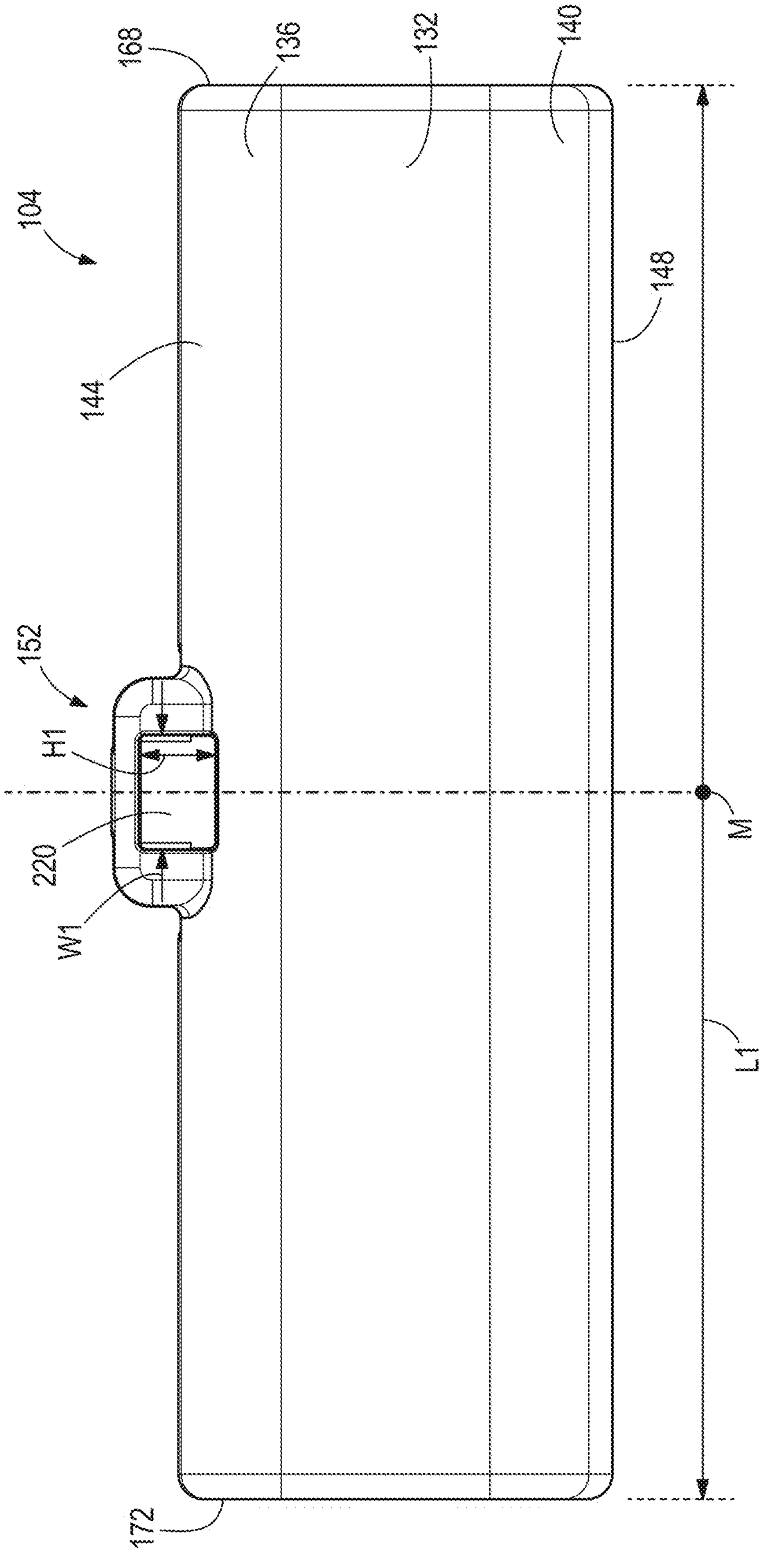
FIG. 3 is a side view of one of a pair of sternal plates of the thoracic device of FIG. 2.

FIG. 3 illustrates the sternal plate including a fifth end 168 and a sixth end 172 that define a length L1 measured therebetween. In the illustrated embodiment, the length L1 is 113 millimeters. In other embodiments, the length L1 is between 13 millimeters and 160 millimeters. In the illustrated embodiment, the ends 168, 172 include fillets to reduce irritation when interacting with sternal edges 116 of the patient. In the illustrated embodiment, each sternal plate of the pair of sternal plates 104 have a common length L1. In other words, each sternal plate of the pair of sternal plates 104 are the same length. In other embodiments, sternal plates of the pair of sternal plates 104 have a different length L1. A center of the cavity 152 is located at a midpoint M of the length L1. In other embodiments, the cavity 152 is disposed on the first arm 144 proximal to first end 136. In other embodiments, the cavity 152 is disposed on the first arm 144 proximal to the second end 140. The cavity 152 includes a height H1 and width W1. In the illustrated embodiment, the height H1 is approximately 6 millimeters and the width is approximately 9 millimeters.

Figure 4:
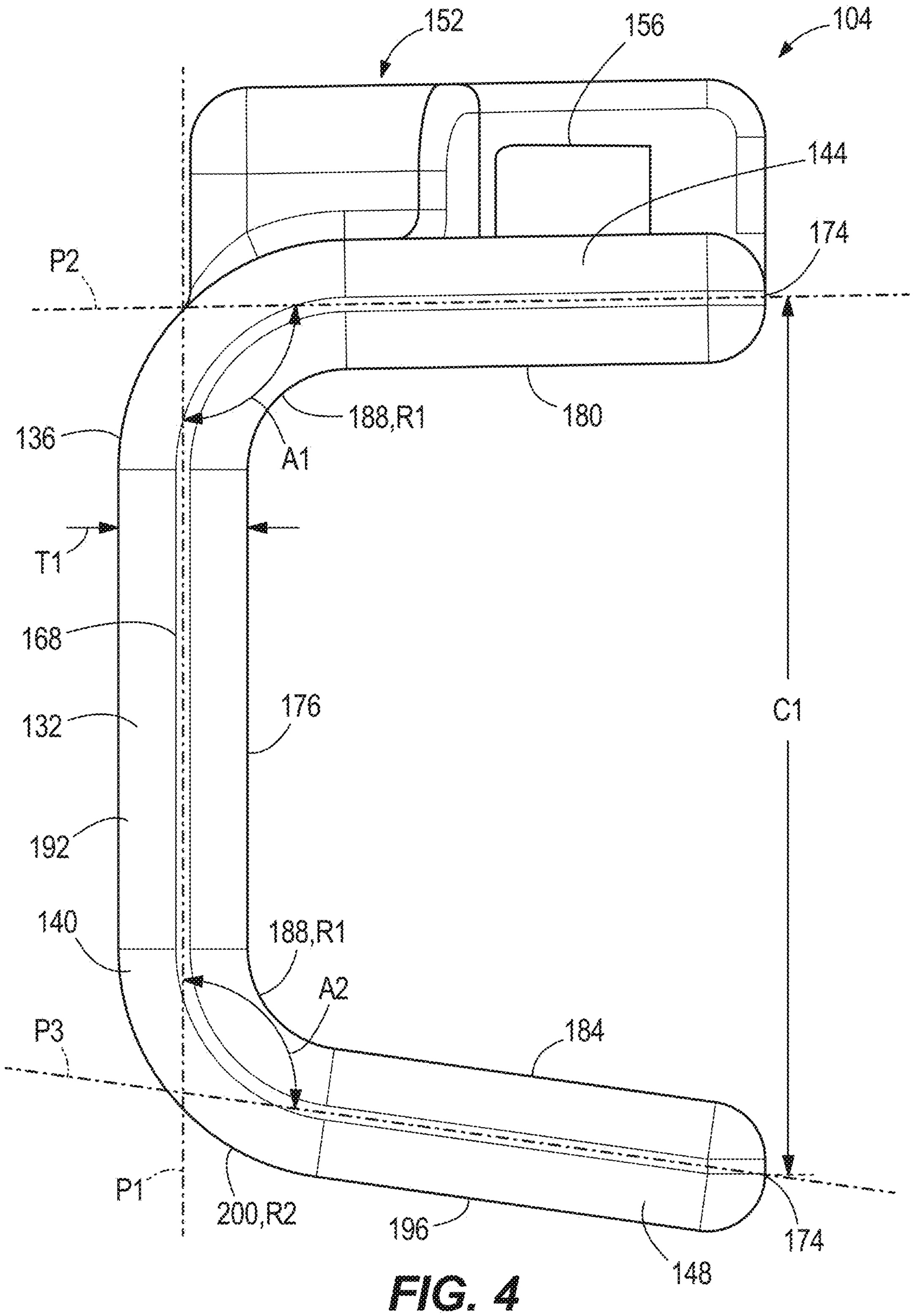
FIG. 4 is a front view of the one of the pair of sternal plates of FIG. 3.

FIG. 4 illustrates the body 132 of the sternal plate defining a first plane P1. The first arm 144 defines a second plane P2 and the second arm 148 defines a third plane P3. The second plane P2 is separated by a non-zero angle A1 relative to the first plane P1. In the illustrated embodiment, the non-zero A1 is 91 degrees. In other embodiments, the non-zero angle A1 is between 90 and 110 degrees. The third plane P3 is separated by a non-zero angle A2 relative to the first plane P1. In the illustrated embodiment, the non-zero angle A2 is 98 degrees. In other embodiments, the non-zero angle A2 is between 90 and 110 degrees. The body 132 defines a thickness T1. In the illustrated embodiment, the thickness T1 is approximately 4.5 millimeters. In other embodiments, the thickness T1 is between 1 millimeter and 6 millimeters. In the illustrated embodiment, a thickness defined by the first and second arms 144, 148 is the same thickness as the thickness T1.

Figure 12:
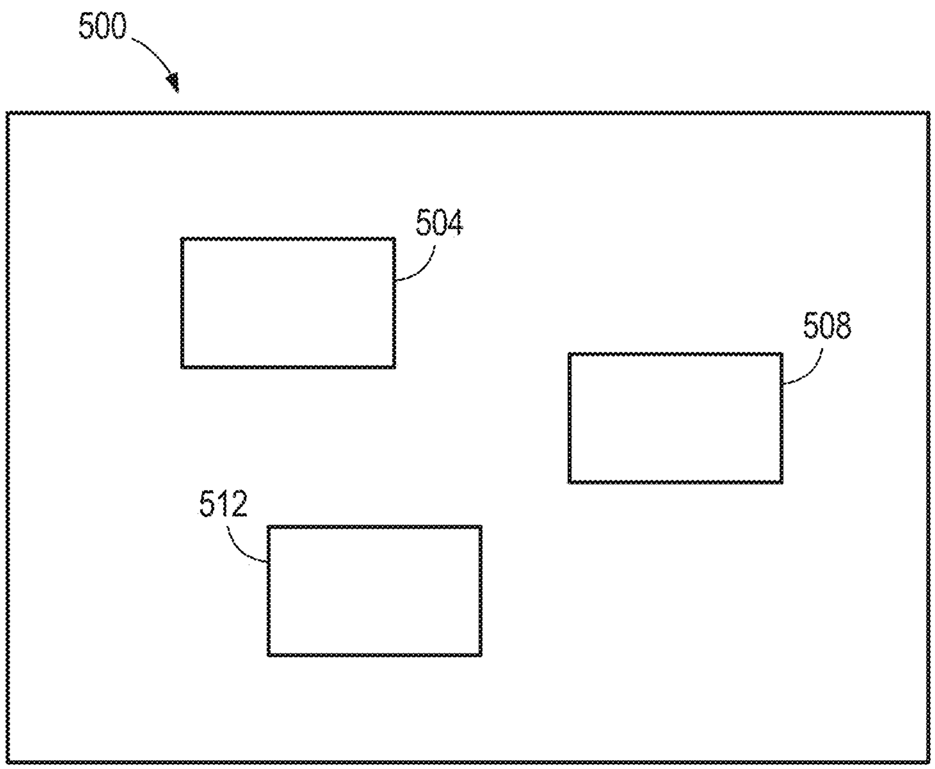
FIG. 12 is a schematic view of a kit, according to an embodiment of the disclosure.

The first and second arms 144, 148 define a clearance C1 that receives a sternal edge of the sternal edges 116. The clearance C1 is measured from the second plane P2 to the third plane P3 at ends 174 of the first and second arms 144, 148. In the illustrated embodiment, the clearance C1 is approximately 30 millimeters. In other embodiments, the clearance C1 is between 10 and 40 millimeters. Similar to the ends 168, 172, the ends 174 includes fillets. A sternal surface 176 of the body 132 contacts the sternal edge (FIG. 1). A surface 180 of the first arm 144 contacts the chest 112 and a surface 184 of the second arm 148 contacts an interior of the chest 112 (FIG. 12). The sternal plate includes a fillet 188 between the sternal surface 176 and the surfaces 180, 184. In the illustrates embodiment, the fillet 188 has a radius R1 of 3.5 millimeters. In other embodiments, the radius R1 is between 1 millimeter and 6 millimeters. A thoracic surface 192 of the body 132 is adjacent the space 128 (FIG. 1) and a surface 196 of the second arm 148 facing the chest cavity 126. The sternal plate includes a fillet 200 between the thoracic surface 192 and the surface 196. In the illustrated embodiment, the fillet 200 has a radius R2 of 8 millimeters. In other embodiments, the radius of the fillet 200 is between 4 and 14 millimeters. In the case of myocardial edema (FIG. 1), the fillet 200 ensures that a smooth surface is in contact with the heart 124. In other words, the thoracic device 100 includes smooth surfaces in contact with the chest 112 or the chest cavity 126.

Figure 5:
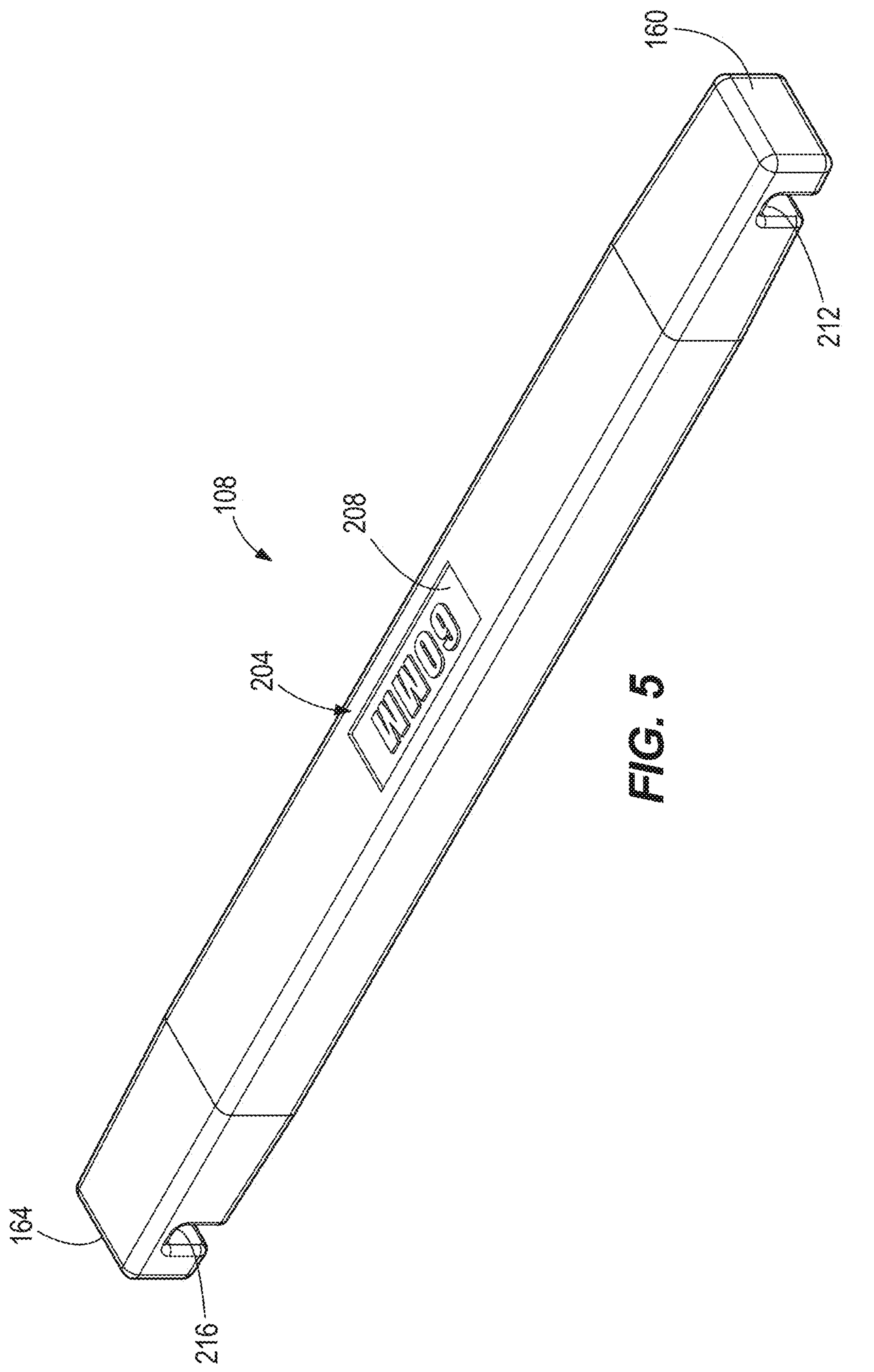
FIG. 5 is a front perspective view of a bar of the thoracic device of FIG. 2.
Figure 6:
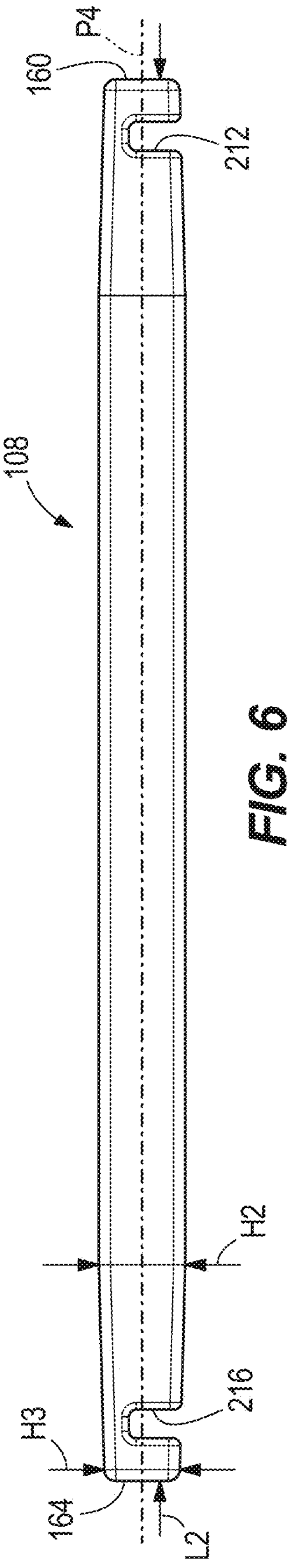
FIG. 6 is a side view of the bar of FIG. 5.

FIGS. 5 and 6 illustrate the bar 108 including a length L2 defined between the third end 160 and the fourth end 164. In the illustrated embodiment, the length L2 is approximately 97 millimeters. In other embodiments, the length L2 is between 34 millimeters and 160 millimeters. The bar 108 includes an indicator 204 (FIG. 2) that identifies a distance D1 (FIG. 2) between each thoracic surface 192 of the pair of sternal plates 104. In the illustrated embodiment, the distance D1 is 60 millimeters. In some embodiments, the indicator 204 includes a radiopaque marker. In other embodiments, the bar 108 includes other radiopaque markers in addition to the indicator 204 to aid in radiographic positioning of the patient. In other embodiments, the distance D1 is between 0 (i.e., there is no distance between each thoracic surface 192 of the pair of sternal plates 104) and 160 millimeters. The indicator 204 provides an approximation of the distance between the sternal edges 116 of the patient. In the illustrated embodiment, the indicator 204 is located at a midpoint of the length L2. In other embodiments, the indicator 204 is disposed closer to the third end 160. In other embodiments, the indicator 204 is disposed closer to the fourth end 164. In the illustrated embodiment, the indicator 204 is raised relative to a recess 208 of the bar 108 and displays “60 MM.” In other embodiments, the indicator 204 may display text identifying the distance D1 between 0 millimeters and 160 millimeters. In other embodiments, the indicator 204 identifies a distance D2 between the sternal surface 176 of the pair of sternal plates 104. In other words, the indicator 204 identifies the true distance between the sternal edges 116 (e.g., the distance D2). The third end 160 of the bar 108 includes a first channel 212 and the fourth end 164 includes a second channel 216. The first and second channels 212, 216 extend entirely through the bar 108.

Figure 7:
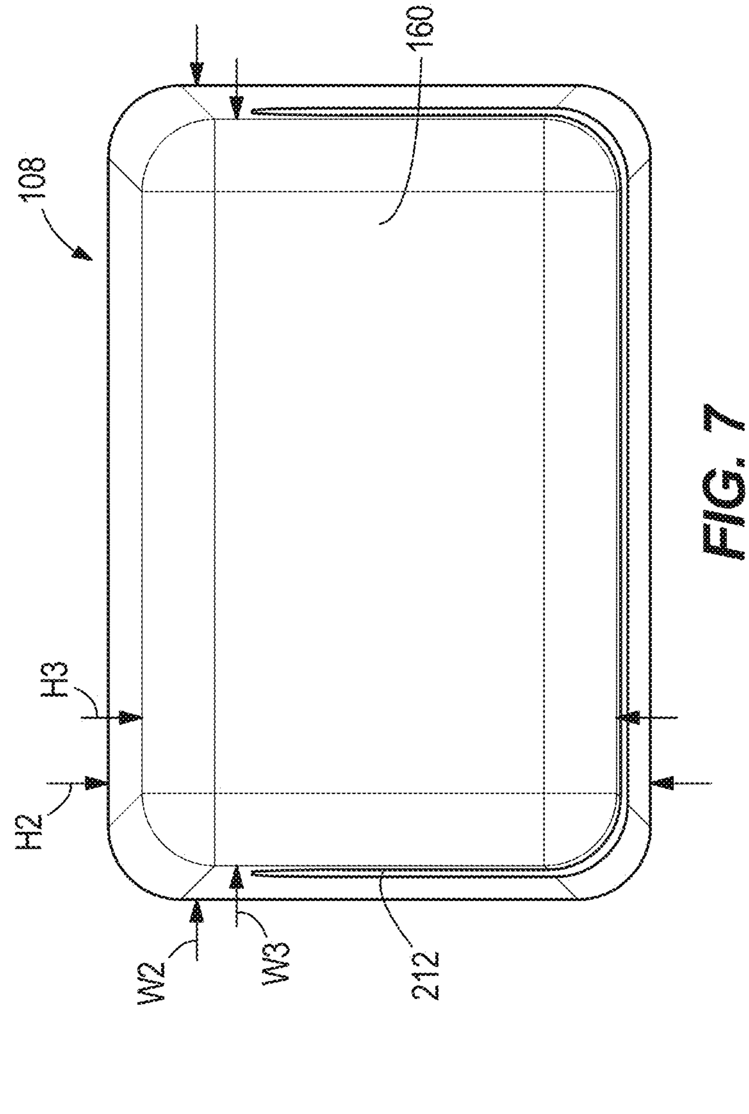
FIG. 7 is a front view of the bar of FIG. 5.

FIG. 7 illustrates the bar 108 defining a height H2 and a width W2. In the illustrated embodiments, the height H2 is approximately 6 millimeters and the width is approximately 9 millimeters. Each of the ends 160, 164 include a height H3 and a width W3. In the illustrated embodiment, the height H3 is approximately 5 millimeters and the width W3 is approximately 8 millimeters. The height H3 and width W3 of the ends 160, 164 are smaller than the corresponding height H2 and width W2 such that the ends 160, 164 are easily received within the respective cavity 152 of the pair of sternal plates 104. The bar 108 includes a draft at the ends 160, 164 of the bar 108 that span the difference in heights H2, H3 and the difference in widths W2, W3.

Figure 8:
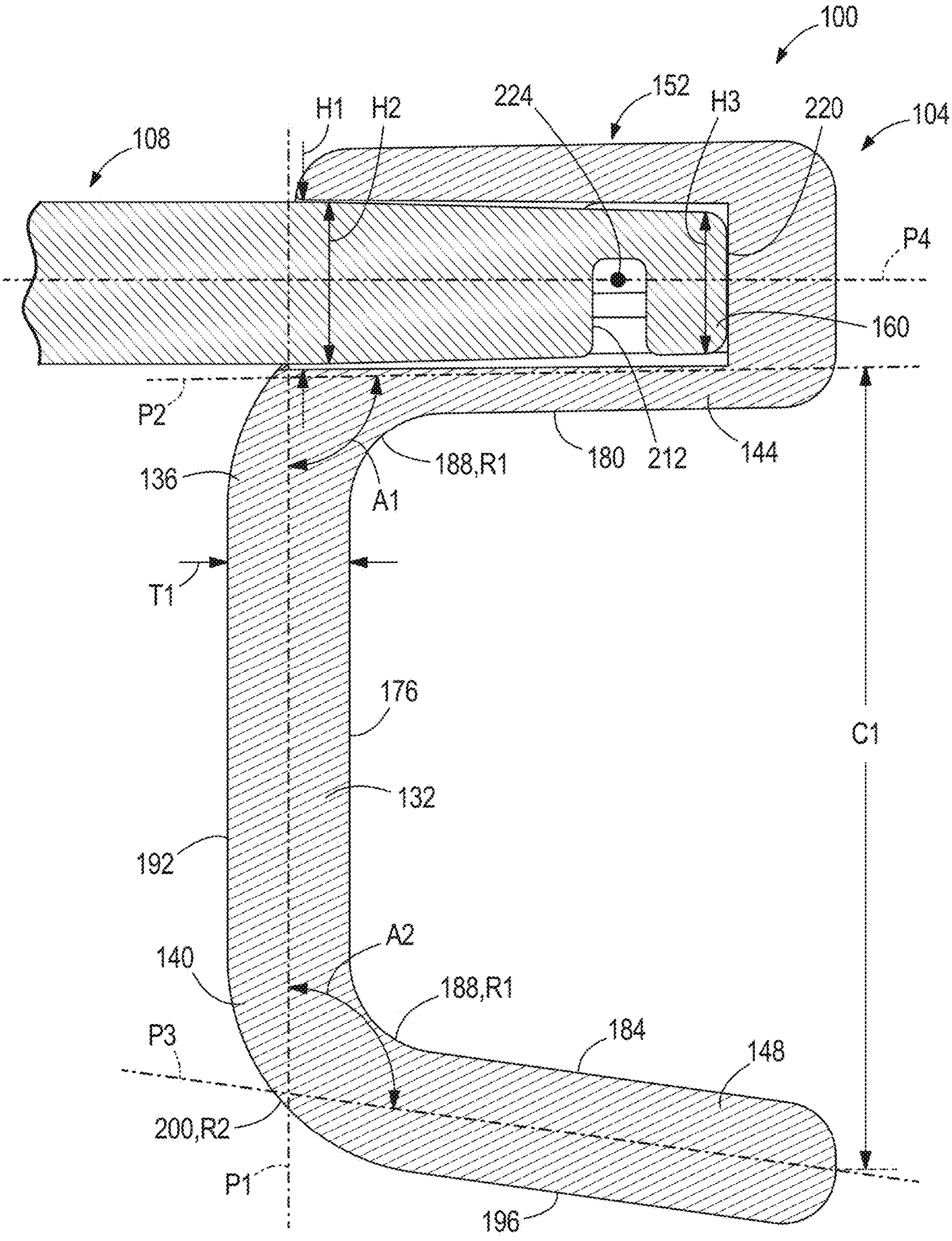
FIG. 8 is a cross-sectional view of the thoracic device taken at lines 8-8 of FIG. 2.

FIG. 8 illustrates the third end 160 of the bar 108 received by the cavity 152 of the sternal plate of the pair of sternal plates 104. The bar 108 is considered fully inserted into the cavity 152 when the third end 160 contacts a surface 220 of the cavity 152. When the third end 160 is fully inserted, the first channel 212 and the aperture 156 overlap along an axis O (FIG. 2). The fourth end 164 is received in a similar manner to the cavity 152 of the other sternal plate of the sternal plates 104. The bar 108 defines a plane P4 that is perpendicular to the plane P1.

Figure 9:
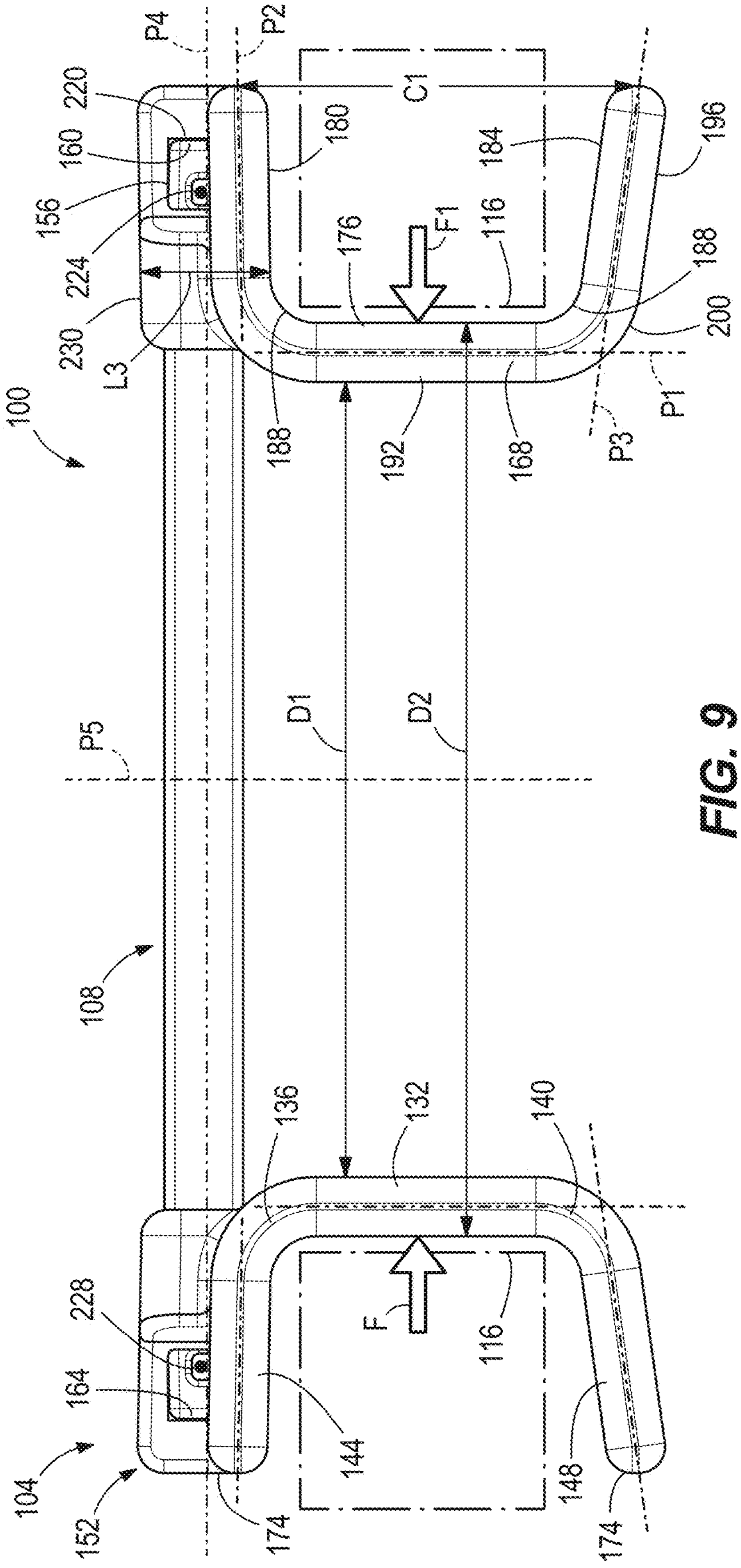
FIG. 9 is a front view of the thoracic device of FIG. 2.

FIG. 9 illustrates the thoracic device 100 assembled together with the sternal edges 116 of the patient schematically illustrated. The sternal edges 116 of the patient induce a force F that is directed toward a central plane P5, which is the approximate center of the chest 112 of the patient (FIG. 1). The force F causes the ends 160, 164 of the bar 108 to remain in contact with the cavity 152 of each respective sternal plate. Optionally, the thoracic device 100 includes a fastener 224 that extends through the first channel 212 and the cavity 152 along the axis O. The fastener 224 couples the third end 160 of the bar 108 to the sternal plate of the pair of sternal plates 104 such that the third end 160 and the sternal plate are in a locked configuration. In the locked configuration, the third end 160 and the sternal plate cannot separate from one another. In some embodiments, the fastener 224 can be coupled to the sternal edges 116 of the patient in the locked position. For instance, the fastener 224 can be sutured to the sternal edges 116 of the patient. In the illustrated embodiment, the fastener 224 is surgical wire. In other embodiments, the fastener 224 includes corresponding dimensions with the first channel 212 such that the sternal plate of the pair of sternal plates 104 cannot be axially moved along the plane P4. In contrast, the surgical wire has a diameter that is smaller than the first channel 212 which enables movement of the third end 160 or the sternal plate along the plane P4. Optionally, the thoracic device 100 includes a fastener 228 that extends through the channel 216 and the cavity 152 along the axis O. The fastener 228 couples the fourth end 164 of the bar 108 to the other sternal plate of the pair of sternal plates 104 such that the fourth end 164 and the sternal plate are in the locked configuration. In some embodiments, the fastener 228 can be coupled to the sternal edges 116 of the patient in the locked position. For instance, the fastener 228 can be sutured to the sternal edges 116 of the patient. In the illustrated embodiment, the fastener 228 is surgical wire. In other embodiments, the fastener 224 includes corresponding dimensions with the channel 216 such that the sternal plate of the pair of sternal plates 104 cannot be axially moved along the plane P4.

The thoracic device 100 includes a surface 230 that is disposed on the cavity 152. A length L3 between the surface 180 and the surface 230 approximately illustrates the amount of material extending from an outer surface of the chest 112. In other words, the length L3 approximates an outer profile of the thoracic device 100 that outward relative to the outer surface of the chest 112. Since the surface 180 is contacts an outer surface of the chest 112, it can be used as a reference for the outer surface of the chest. In the illustrated embodiment, the length L3 is approximately 10 millimeters. In other embodiments, the length L3 is between 4 millimeters and 15 millimeters.

Figure 10:
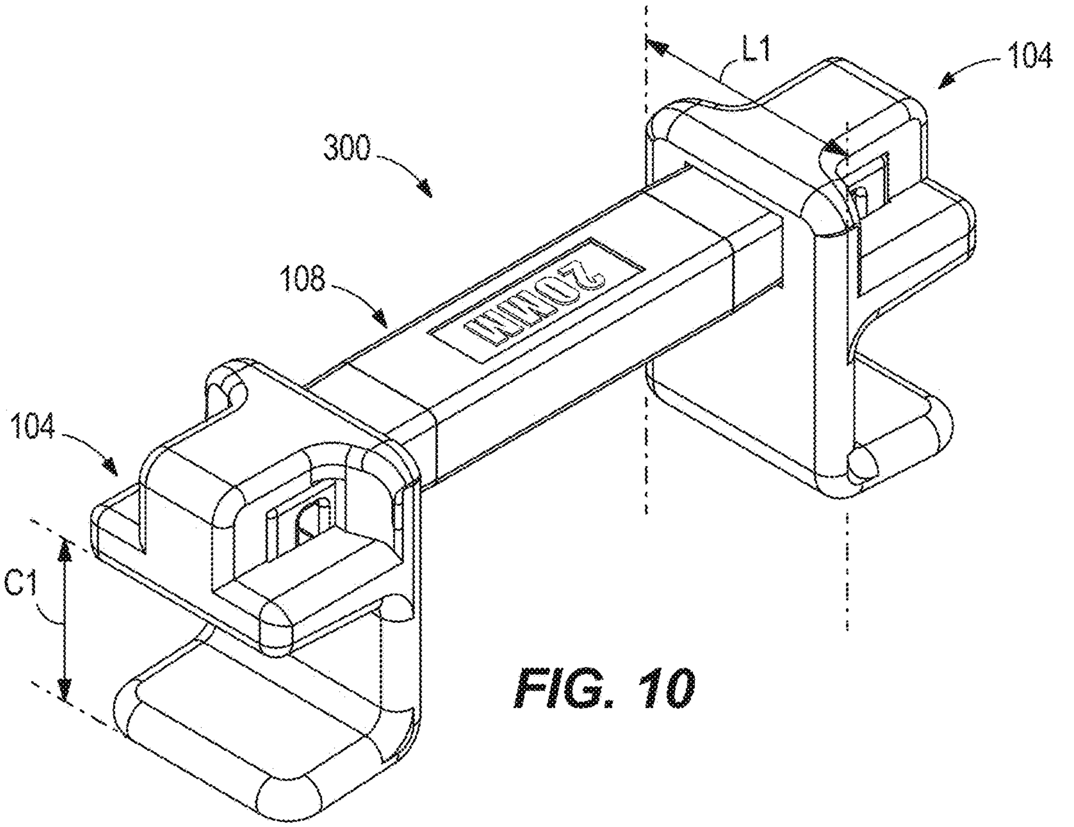
FIG. 10 is a perspective view of a thoracic device, according to an embodiment of the disclosure.

FIG. 10 illustrates another embodiment of a thoracic device 300 with like features as the thoracic device 100 being identified with like reference numerals. Since the thoracic device 300 is like the thoracic device 100, only differences will be discussed. Specifically, the thoracic device 300 includes different dimensions for the pair of the sternal plates 104 and the bar 108. In the illustrated embodiment, the length L1 is approximately 18 millimeters and the clearance C1 is approximately 15 millimeters. The length L2 of the bar 108 is approximately 57 millimeters and includes an indicator 204 identifying "20 millimeters."

Figure 11:
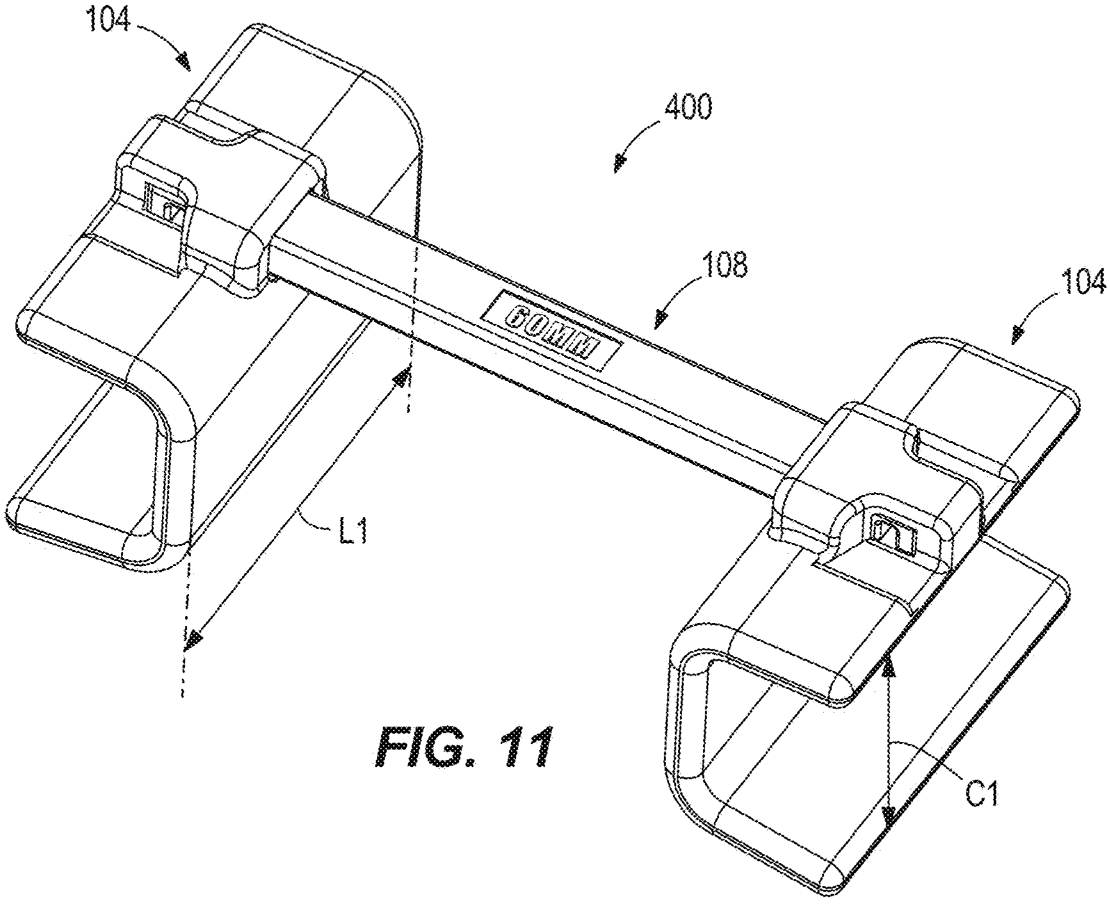
FIG. 11 is a perspective view of a thoracic device, according to an embodiment of the disclosure.

FIG. 11 illustrates another embodiment of a thoracic device 400 with like features as the thoracic device 100 being identified with like reference numerals. Since the thoracic device 400 is like the thoracic device 100, only differences will be discussed. Specifically, the thoracic device 400 includes different dimensions for the pair of the sternal plates 104 and the bar 108. In the illustrated embodiment, the length L1 is approximately 53 millimeters and the clearance C1 is approximately 29 millimeters. The clearance C1 of the thoracic device 400 is greater than the clearance C1 of the thoracic device 300.

The thoracic devices 100, 300, and 400 illustrate that the dimensions of the pair of sternal plates 104 and the bar 108 can change depending on patient or procedure. For instance, the dimensions of the thoracic device 300 may be suited for an infant whereas the dimensions of the thoracic device 100 may be suited for an adult. As such, a variety of dimensions for the pair of sternal plates 104 and the bar 108 is necessary for compatibility with patients and procedures.

FIG. 12 illustrates a kit 500 including a first pair of sternal plates 504 and a plurality of bars 508. The first pair of sternal plates 504 is the pair of sternal plates 104. Each of the plurality of bars 508 are the bar 108 with a different value of the length L2 and the indicator 204. For instance, a first bar of the plurality of bars 508 includes the length L2 of 97 millimeters and the indicator 204 identifying 60 millimeters (e.g., the bar 108 in FIGS. 2 and 11). A second bar of the plurality of bars 508 includes the length L2 of 57 millimeters and the indicator 204 identifying 20 millimeters (e.g., the bar 108 in FIG. 10). The plurality of bars 508 may include additionally bars each having varying length L2 between 37 millimeters and 160 millimeters and the indicator 204 displaying text identifying the distance D1 between 0 millimeters and 160 millimeters. A bar of the plurality of bars 508 can be selected to cooperate with the first pair of sternal plates 504 to form the thoracic device 100 depending on the patient and procedure.

The kit 500 includes a second pair of sternal plates 512. The second pair of sternal plates 512 is the pair of sternal plates 104. The second pair of sternal plates 512 have different dimensions than the first pair of sternal plates 504. For instance, the clearance C1 of the second pair of sternal plates 512 may be larger or smaller than the clearance C1 of the first pair of sternal plates 504. Other differences in dimensions between the first and the second pair of sternal plates 504, 512 may include the length L1, the angle A1, the angle A2, the thickness T1, the radius R1, the radius R2. In the illustrated embodiment, the kit 500 may include additional pairs of plates with varying dimensions, as described above in relation to the second pair of sternal plates 512. Additionally, it is worth noting that although the illustrated thoracic devices (e.g., 100, 300, and 400) have pairs of matching sternal plates, the pair of sternal plates can be mixed and matched with one another. For instance, the third end 160 of a bar of the plurality of bars 508 can be coupled to a sternal plate of the first pair of sternal plates 504 and the fourth end of the bar can be coupled to a sternal plate of the second pair of sternal plates 512. In other words, the sternal plates of the thoracic device can be mismatched.

Figure 13:
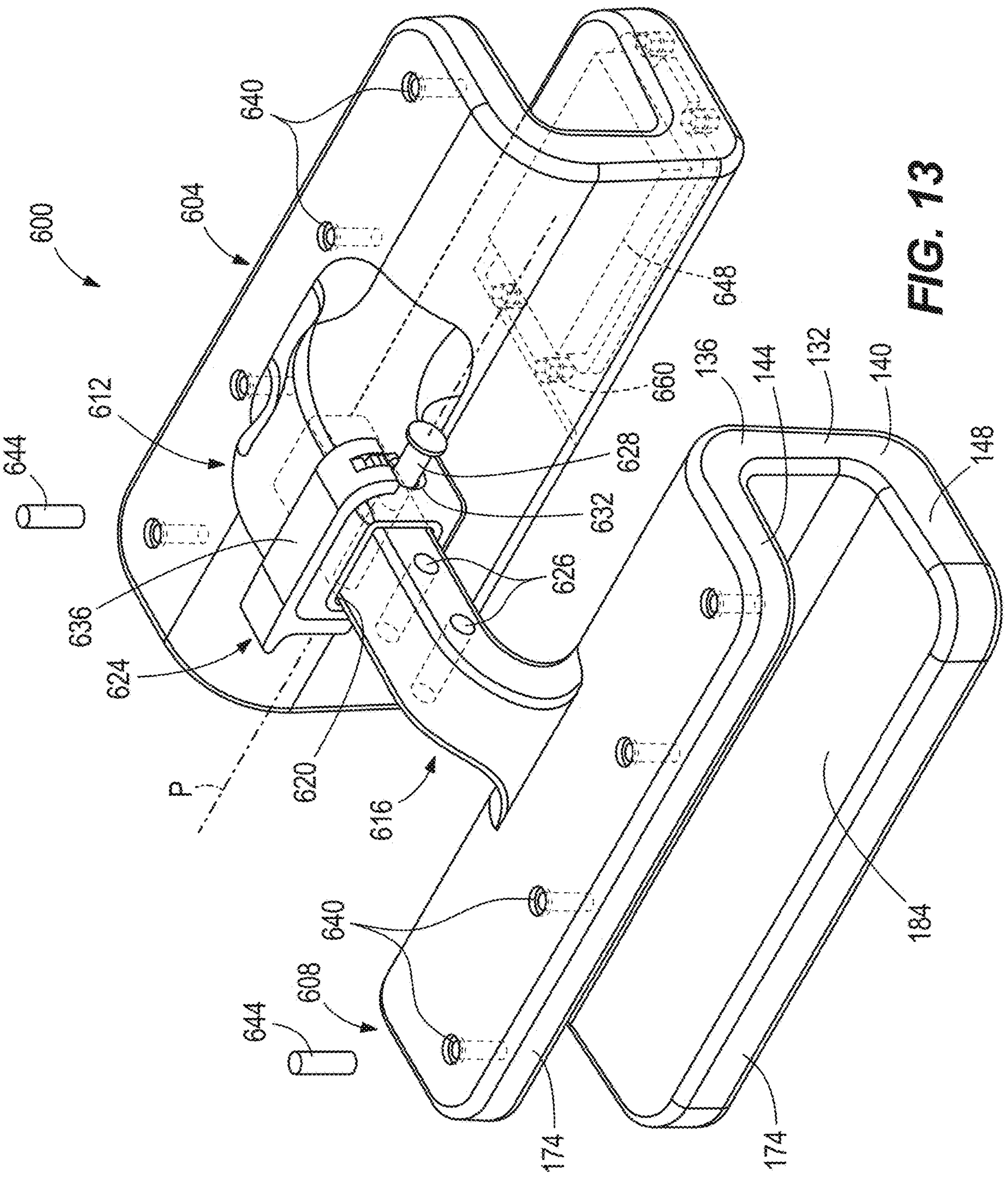
FIG. 13 is a perspective view of a thoracic device, according to an embodiment of the disclosure.
Figure 14:
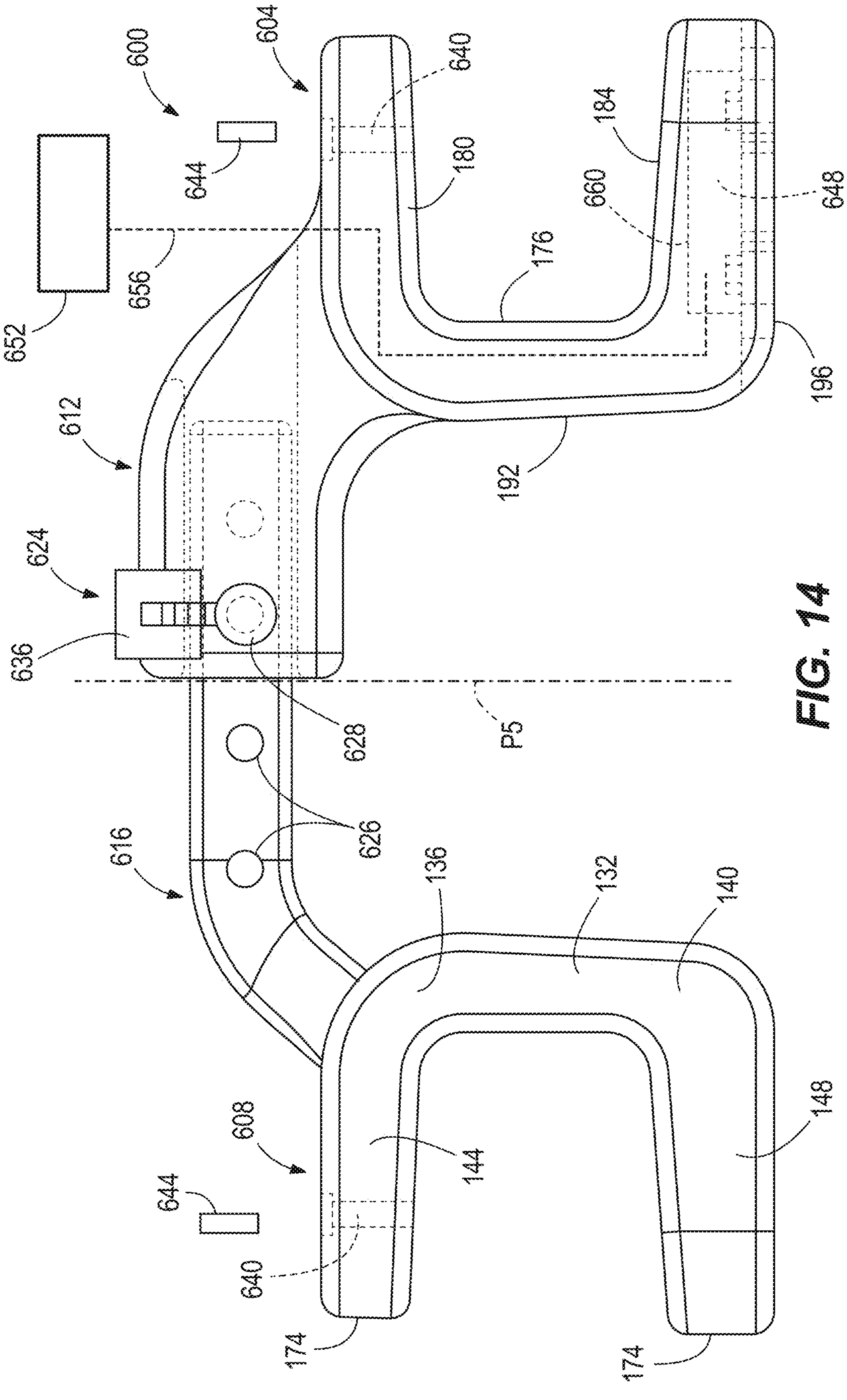
FIG. 14 is a front view of the thoracic device of FIG. 13.

FIG. 13 illustrates another embodiment of a thoracic device 600 with like features as the thoracic device 100 being identified with like reference numerals. Since the thoracic device 600 is like the thoracic device 100, only differences will be discussed. The thoracic device 600 includes a first sternal plate 604 and a second sternal plate 608. The first sternal plate 604 includes a cavity 612 configured to receive a bar 616 of the second sternal plate 608. The bar 616 is integrated with the second sternal plate 608. The cavity 612 protrudes from the first arm 144 of the first sternal plate 604 toward the central plane P5. The cavity 612 includes a first aperture 620 which receives the bar 616. The thoracic device 600 further includes a pin 624 used for coupling the first sternal plate 604 to the second sternal plate 608. Specifically, the bar 616 is fastened to the cavity 612. The pin 624 includes a body 628 that is received by a second aperture 632 of the cavity 612 and an aperture of a plurality of apertures 626 of the bar 616 in a locking configuration (e.g., the first and second sternal plates 604, 608 are fixed relative to one another). The apertures of the plurality of apertures 626 are staggered axially along the plane P4 such that the distance D1 may be adjusted (FIG. 14). The pin 624 includes a locking mechanism 636 for preventing the pin 624 from axially moving along a pin axis P. In the illustrated embodiment, the locking mechanism is a hinge pivotally coupled to the body 628 and includes a protrusion engaging the cavity 612, thereby preventing axial movement of the body 628 along the axis P.

FIG. 14 illustrates the first and second sternal plates 604, 608 including apertures 640. Optionally, the apertures 640 receive fasteners 644 that couple the first and second sternal plates 604, 608 to respective sternal edges 116. In some embodiments, holes corresponding to the apertures 640 are drilled into the sternal edges 116 and the fasteners 644 (e.g., screws) couple the first and second sternal plates 604, 608 to the sternal edges 116. The thoracic device 600 further includes a transducer 648. In the illustrated embodiment, the transducer 648 is used for generating and sensing ultrasound energy for ultrasonic imaging. The transducer 648 is coupled to a controller 652, which is programmed with an algorithm for controlling the transducer 648 and analyzing signals from the transducer 648. Optionally, the thoracic device includes a wire 656 that couples the transducer 648 to the controller 652. The wire 656 permits communication between the transducer 648 and the controller 652 and supplies power from the controller 652 to the transducer 648. In other embodiments, the transducer 648 wirelessly communicates with the controller 652. In the illustrated embodiment, the transducer 648 is received within a recess 660 of the second arm 148 of the first sternal plate 604. In other embodiments, the transducer 648 is received by the second arm 148 of the second sternal plate 608. The recess 660 is disposed proximal to the fifth end 168.

Figure 15:
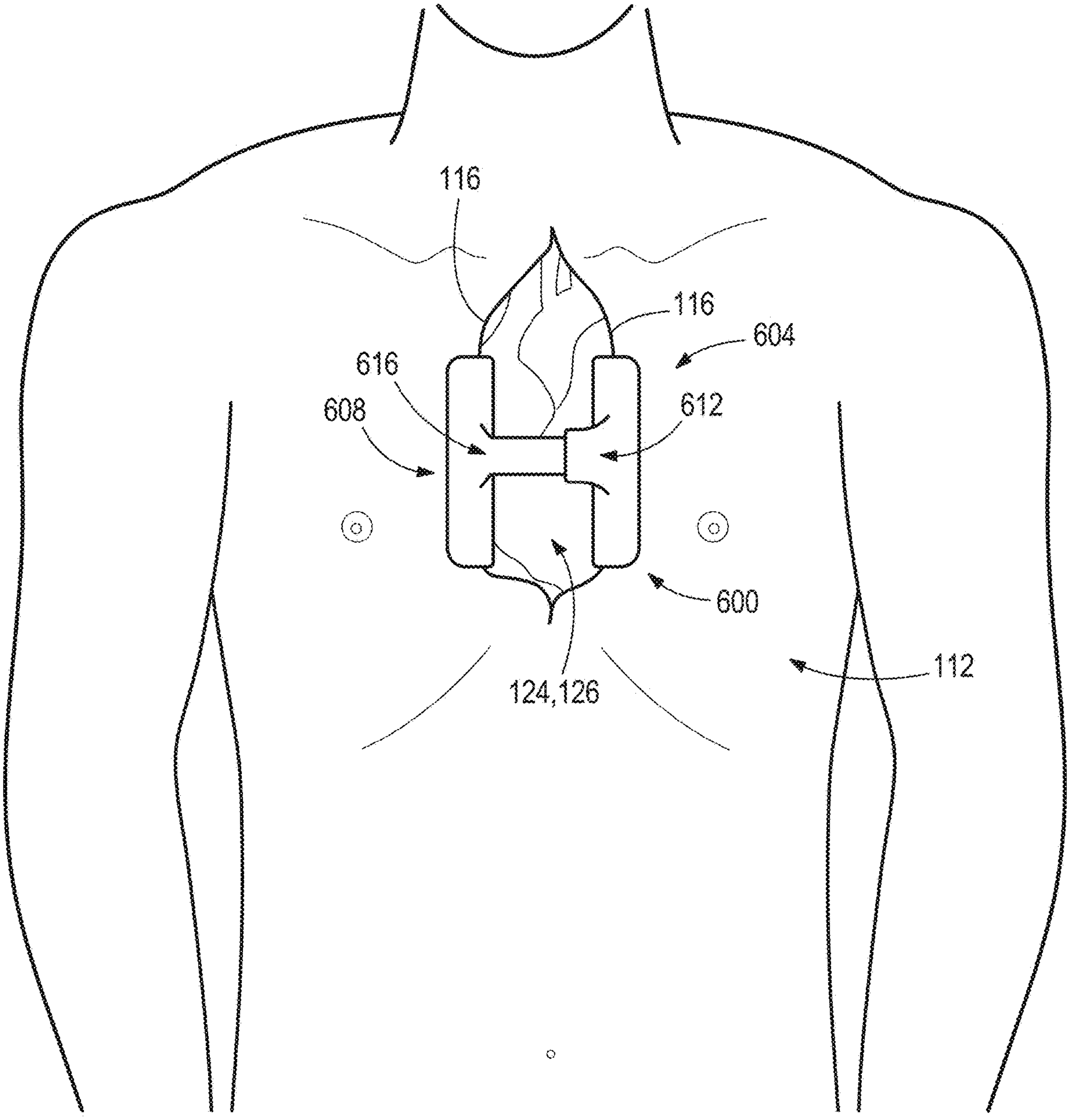
FIG. 15 is a schematic view the thoracic device of FIG. 13.
Figure 16:
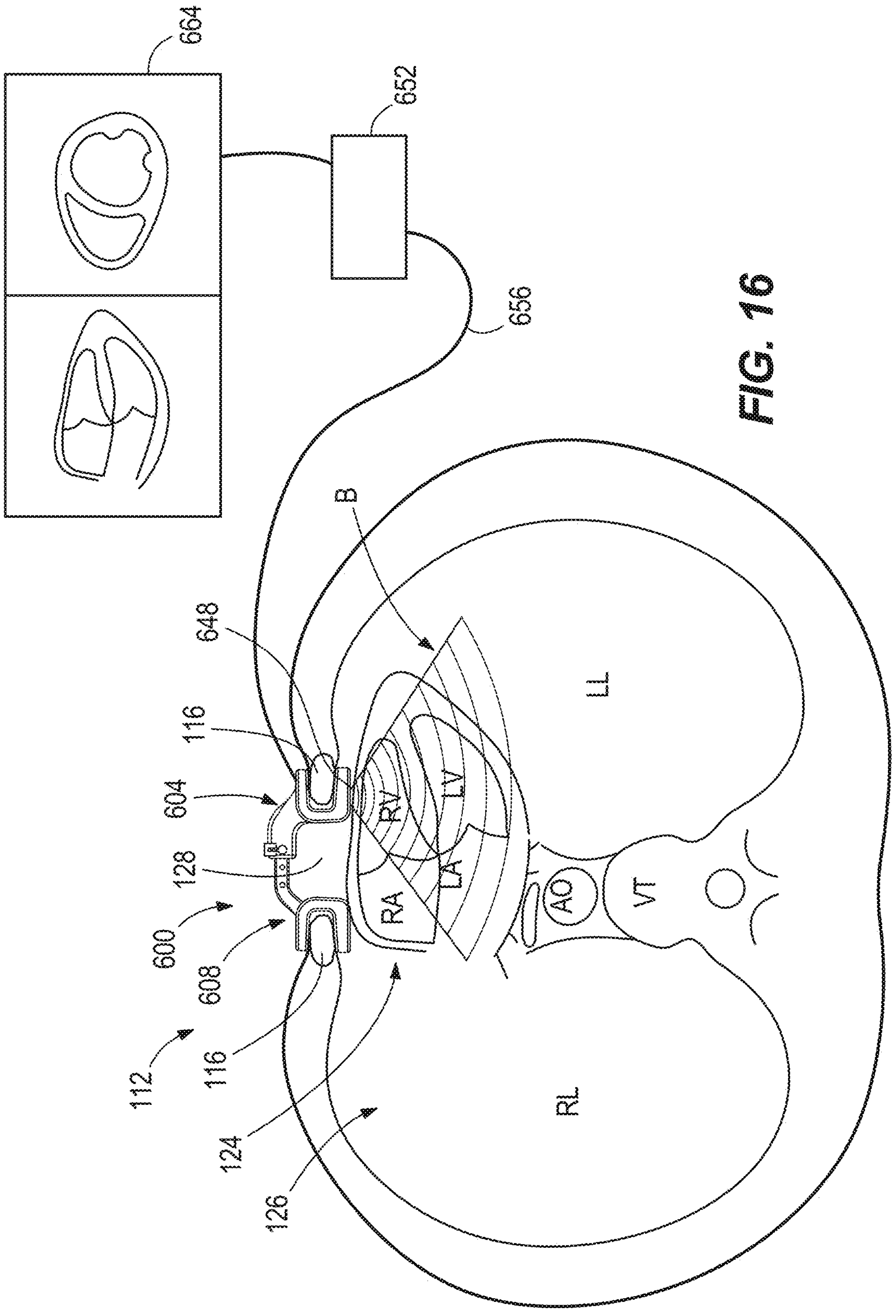
FIG. 16 is a schematic view the thoracic device of FIG. 13.

FIGS. 15 and 16 schematically illustrate the thoracic device 600 holding the sternal edges 116. As shown in FIG. 16, the transducer 648 generates and directs ultrasound energy B within the chest cavity 126. In the illustrated embodiment, the beam B is directed toward the heart 124. The transducer 648 detects and send signals to the controller 652 via the wire 656. The algorithm of the controller 652 analyzes the signals from the transducers and outputs a signal to a display 664. Although the transducer 648 and the controller 652 are solely illustrated with respect to the thoracic device 600, the transducer 648 and the controller 652 are compatible with the thoracic device 100.

In the illustrated embodiment, the transducer 648 is a matrix transducer capable of orthogonal as well as 3-dimensional cardiac imaging. The matrix transducer provides orthogonal imaging that allows for internal alignment and steering of the ultrasound energy B to interrogate specific heart structures of interest.

Although the disclosure has been described in detail with reference to certain preferred embodiments, variations and modifications exist within the scope and spirit of one or more independent aspects of the disclosure as described.

Various features of the disclosure are set forth in the following claims.

What is claimed is:

1. A thoracic device comprising:

a pair of sternal plates, each sternal plate of the pair of sternal plates including a body having a first end and a second end, a first arm extending from the first end of the body, the first arm having a cavity oriented transverse to the body and an aperture oriented parallel to the body, and a second arm extending from the second end of the body, the first arm having an inner surface facing the second arm and an outer surface opposite the inner surface, the cavity disposed on the outer surface, the aperture passing through the outer surface into the cavity; and a bar including a third end and a fourth end and defining a longitudinal axis extending through the third end and the fourth end, the third end having a first channel extending through the bar and the fourth end having a second channel extending through the bar, wherein the third end of the bar is received within the cavity of one of the pair of sternal plates along the longitudinal axis and the fourth end of the bar is received within the cavity of the other of the pair of sternal plates along the longitudinal axis, and wherein, when the third end of the bar is received within the cavity, the first channel and the aperture are configured to axially align along a fastener axis perpendicular to the longitudinal axis of the bar to receive a fastener therethrough, and wherein the bar is disposed on a side of the first arm opposite the body, and the cavity opens toward the bar.

2. The thoracic device of claim 1, further comprising a fastener configured to couple the third end of the bar to the first arm of the one of the pair of sternal plates.

3. The thoracic device of claim 2, wherein the fastener is configured to extend through the aperture of the first arm and the first channel of the bar.

4. The thoracic device of claim 1, wherein the aperture of the first arm and the first channel of the bar are configured to axially overlap.

5. The thoracic device of claim 1, wherein the body defines a plane, wherein the first arm defines a plane, and wherein the plane of the first arm is oriented at a non-zero angle between 90 degrees and 110 degrees relative to the plane of the body.

6. The thoracic device of claim 5, wherein the bar defines a plane, and wherein the plane of the body and the plane of the bar are perpendicular.

7. The thoracic device of claim 1, wherein the body defines a plane, wherein the second arm defines a plane, and wherein the plane of the second arm is oriented at a non-zero angle between 90 degrees and 110 degrees relative to the plane of the body.

8. The thoracic device of claim 1, wherein the bar includes a length defined between the third end of the bar and the fourth end of the bar, and wherein the length is between 37 millimeter and 160 millimeters.

9. The thoracic device of claim 1, wherein the bar includes an indicator displaying a distance between a first sternum edge of a patient and a second sternum edge of a patient.

10. The thoracic device of claim 1, wherein the pair of sternal plates and the bar are comprised of a partially radiopaque glass reinforced polymer.

11. The thoracic device of claim 1, wherein the cavity is disposed at a midpoint of the first arm, and wherein the outer surface of the first arm defines a pair of notches disposed on opposite sides of the aperture.

12. The thoracic device of claim 1, wherein the second arm includes a transducer configured to generate and sense ultrasound energy.

13. A kit comprising:

- a first pair of sternal plates, each of the first pair of sternal plates including
  - a body having a first end and a second end, the body having a first length,
  - a first arm extending from the first end of the body, the first arm having a cavity oriented transverse to the body and an aperture oriented parallel to the body, and
  - a second arm extending from the second end of the body, the first arm having an inner surface facing the second arm and an outer surface opposite the inner surface, the cavity disposed on the outer surface, the aperture passing through the outer surface into the cavity; and
- a plurality of bars, each bar having a different length and defining a longitudinal axis, each bar including
  - a third end and a fourth end, the longitudinal axis extending through the third end and the fourth end, the third end having a first channel extending through the bar and the fourth end having a second channel extending through the bar,
- wherein the third end of the bar is received within the cavity of one of the first pair of sternal plates along the longitudinal axis and the fourth end of the bar is received within the cavity of the other of the first pair of sternal plates along the longitudinal axis, such that the bar is disposed on a side of the first arm opposite the body of each of the first pair of sternal plates, and
- wherein, when the third end of the bar is received within the cavity, the first channel and the aperture are configured to axially align along a fastener axis perpendicular to the longitudinal axis of the bar to receive a fastener therethrough.

14. The kit of claim 13 further comprising:

- a second pair of sternal plates, each of the second pair of sternal plates including
- a body having a first end and a second end, the body having a second length different than the first length of the body of the first pair of sternal plates,
- a first arm extending from the first end of the body, the first arm having a cavity oriented transverse to the body and an aperture oriented parallel to the body, and
- a second arm extending from the second end of the body.

15. The kit of claim 14, wherein the first arm and the second arm of the first pair of sternal plates define a first clearance configured to receive a sternum edge of a patient.

16. The kit of claim 15, wherein the first arm and the second arm of the second pair of sternal plates define a second clearance configured to receive a sternum edge of a patient, and wherein the first clearance is greater than the second clearance.

17. The kit of claim 13, wherein each bar includes a length between the third end and the fourth end, and wherein the length of each bar is between 37 millimeter and 160 millimeters.

18. The kit of claim 13, wherein each sternal plate of the first pair of sternal plates includes

- a first plane defined by the body,
- a second plane defined by the second arm,
- wherein the second plane is oriented at a non-zero angle between 90 degrees and 110 degrees relative to the first plane.

19. The kit of claim 18, wherein each sternal plate of the first pair of sternal plates includes

- a third plane defined by the first arm,
- wherein the third plane is oriented at a non-zero angle between 90 degrees and 110 degrees relative to the first plane.

20. The kit of claim 13, wherein the second arm of the one of the first pair of sternal plates further comprises a transducer configured to generate and sense ultrasound energy.

* * * * *